United States Patent [19]

Fisher

[11] Patent Number: 5,110,731
[45] Date of Patent: May 5, 1992

[54] SYSTEM FOR BIOTIN SYNTHESIS

[75] Inventor: Eric F. Fisher, Boulder, Colo.

[73] Assignee: Amgen, Inc., Thousand Oaks, Calif.

[21] Appl. No.: 537,017

[22] Filed: Jun. 13, 1990

Related U.S. Application Data

[63] Continuation of Ser. No. 983,042, Aug. 12, 1986, abandoned, which is a continuation-in-part of Ser. No. 769,849, Aug. 26, 1985, abandoned.

[51] Int. Cl.$^5$ .................. C12P 17/18; C12N 15/00; C12N 15/70
[52] U.S. Cl. .................. 435/119; 435/172.1; 435/252.33; 435/320.1; 536/27; 935/9; 935/41; 935/60
[58] Field of Search .................. 435/69.1, 172.3, 320, 435/252.3, 117, 172.1, 252.33, 320.1

[56] References Cited

U.S. PATENT DOCUMENTS 4,563,426  1/1986  Yamada .................. 435/244

FOREIGN PATENT DOCUMENTS 0136490  4/1985  European Pat. Off. .
0060996  4/1983  Japan .

OTHER PUBLICATIONS

Bernard, H.-U., et al., 1979, Gene 5:54-76, "Construction of Plasmid Cloning Vehicles that Promote Gene Expression from the Bacteriophage Lambda PL Promoter".
Barker et al., Journal of Bacteriology 143(2), pp. 789-800 (1980).
Howard et al., Gene, 35, pp. 321-331 (1985).
Cleary et al., Journal of Bacteriology, 112, pp. 830-839 (1972).
Pai, Journal of Bacteriology, 112(3), pp. 1280-1287 (1972).
Campbell et al., Proc. Natl. Acad. Sci. 69(3), pp. 676-680 (1972).
Mukherjee et al., Plasmids and Transposons, (1980), Academic Press, pp. 379-386.
Barker et al., J. Mol. Biol., 146, 469-492 (1981).
Barker et al., Gene, 13, 89-102 (1981).
Campbell et al., J. Bacteriology, 135(1), 90-98 (1978).
Campbell et al., J. Bacteriology, 142(3), 1025-1028 (1980).
Cicmanec et al., J. Bacteriology, 133(1), 270-278 (1978).
Cohen et al., Molec. gen. Genet., 166, 305-312 (1978).
Covarrubias et al., Gene, 17, 79-89 (1982).
DasGUPTA et al., Gene, 3, 233-246 (1978).
Del Campillo-Campbell et al., Meth. Enzy., 62, 379-385 (1979).
Drexler, Molec. gen. Genet., 152, 59-63 (1977).
Duffy, ed. "Chemicals by Enzymatic and Microbial Processes", Recent Advances, 284-287, Park Ridge, NJ (1980).
Dykhuizen, J. Bacter., 115(2), 662-667 (1973).
Eisenberg et al., J. Bacter., 98(3), 1227-1231 (1969).
Eisenberg et al., J. Bacter., 122(1), 66-72 (1975).
Eisenberg, "Biotin: Biogenesis, Transport, and Their Regulation", New York, NY, 317-372. In A. Meister ed., Advances in enzymology, vol. 28, John Wiley and Sons, Inc. (1973).
Frapier et al., J. Org. Chem., 47, 2257-2261 (1982).
Hanahan, J. Mol. Biol., 166, 557-580 (1983).
Kaiser et al., Science, 223, 249-255 (1984).
Ketner et al., Proc. Nat'l. Acad. Sci. (USA), 71(7), 2698-2702 (1974).
Ketner et al., J. Mol. Biol., 96, 113-27 (1975).
Konopa et al., Gene, 19, 104-108 (1982).
Kotval et al., Gene, 17, 219-222 (1982).
Landy et al., Science, 197, 1147-1160 (1977).
Lichstein et al., J. Bact., 81, 65-69 (1961).

(List continued on next page.)

Primary Examiner—Robert A. Wax
Assistant Examiner—William W. Moore
Attorney, Agent, or Firm—James G. Passé

[57] ABSTRACT

A system for the production of biotin wherein a biotin retention-deficient strain of a cell is transformed with plasmid bearing the biotin gene cluster bio (A, B, F, C and D). The media of cultures of the resulting cells contains enhanced amounts of biotin by comparison with similar constructions in strains capable of biotin retention.

15 Claims, 9 Drawing Sheets

OTHER PUBLICATIONS

McCormick et al., Anal. Biochem., 34, 226-236 (1970).
Nath et al., Proc. Nat'l. Acad. Sci. (USA), 79, 1786-1790 (1982).
Otsuka et al., Nature, 276, 689-694 (1978).
Oura et al., J. Inst. Brew., 88, 299-308 (1982).
Pai et al., Biochimica et Biophysica Acta, 100, 28-35 (1965).
Pai. J. Bacter., 116(1), 494-496 (1973).
Pai, Molec. Gen. Genet., 134, 345-357 (1974).
Pai et al., Can. J. Microbiol., 21, 1116-1120 (1975).
Piffeteau et al., Biochimica et Biophysica Acta, 688, 29-36 (1982).
Pai et al., Biochim. Biophys, Acta, 100, 43-49 (1965).
Prakash et al., J. Bacter., 120(2), 785-791 (1974).
Prakash et al., J. Bacter., 134(3), 1002-1012 (1978).
Rolfe et al., J. Bacter., 96(2), 515-524 (1968).
Salib et al., Biochem. Biophys. Res. Comm., 88(1), 312-319 (1979).
Salib et al., Chem. Mikrobiol. Technol. Lebensm, 6 99-102 (1980).
Sancar et al., J. Mol. Biol., 148, 63-76 (1981).
Sancar et al., Cell., 28, 523-530 (1982).
Szybalski et al., Gene, 19, 93-103 (1982).
Tsuboi et al., Agr. Biol. Chem., 31(10), 1135-1142 (1967).
Yamada et al., Agric. Biol. Chem., 47(5), 1011-1016 (1983).
del Campillo-Campbell, et al., *J. Bacteriology,* 94(6), pp. 2065-2066 (1972).
Cleary, et al., *Proc. Nat'l Acad. Sci.,* (USA), 69(8), pp. 2219-2223 (1972).
Das Gupta, et al., *Gene,* 1, pp. 331-345 (1977).
Mansoor, et al., *Pakistan Journal of Biochemistry,* 1(1-2), pp. 13-15 (1968).

SYSTEM FOR BIOTIN SYNTHESIS

This is a continuation of co-pending U.S. patent application Ser. No. 06/983,042, filed Aug. 12, 1986, and now abandoned, which is in turn a continuation-in-part of U.S. patent application Ser. No. 06/769,849, filed Aug. 26, 1985, now abandoned.

BACKGROUND

The present invention relates in general to systems for the microbial production of biotin and in particular to systems wherein at least a part of the biotin operon is present on a plasmid within a biotin retention-deficient mutant host cell.

Biotin, also known as vitamin H, is probably an essential component of all cells. Some microorganisms, including baker's yeast, and all animals (except the protozoan Tetrahymena) are unable to synthesize biotin effectively and must therefore obtain biotin from their environment in order to survive.

Despite its usefulness in promoting the growth of baker's yeast and as a human and animal food additive, biotin is very expensive to manufacture by presently available, chemical synthetic methods. Furthermore, although beet molasses (containing 0.015–0.15 $\mu$grams of biotin per gram) or other natural sources of biotin may be used to supplement synthetic biotin, there exists a need for other sources.

Due to the ready availability of information regarding the genetic constitution of certain microorganisms which have been reported to contain relatively high concentrations of biotin, a capability for performing genetic manipulations on those microorganisms has developed. It has been reported, for example, that certain chromosomal genes which encode enzymes of the pathway for biotin synthesis may be isolated, amplified and reinserted into host cells of the bacterium *Escherichia coli* (*E. coli*).

More specifically, Mukherjee, et al. in "Plasmids and Transposons," Stuttard, et. al., eds., Academic Press, New York (1980), 379–386 reported isolation of the biotin operon of the *E. coli* K-12 strain from a transducing bacteriophage by means of EcoRI enzyme digestion. A restriction fragment was inserted into a DNA plasmid (pMB8) which was used to transform *E. coli* host cells to provide multiple "extra" copies of the biotin operon genes in these hosts. Mukherjee, et al., however fails to teach or even suggest the use of a biotin retention-deficient mutant genotype host cell. Although enhancement of excretion over a biotin prototroph ("wild type") was reported, this recombinant system has not been applied to large scale commercial production of biotin by fermentation of transformed host cells.

SUMMARY OF THE INVENTION

A system for the production of biotin according to the present invention comprises a cell having a biotin retention-deficient mutant genotype and extrachromosomal DNA, within said cell, encoding at least one gene product of the biotin operon or a functional homolog thereof.

Another aspect of the present invention comprises a method for converting desthiobiotin to biotin wherein a host organism having a biotin retention-deficient mutant genotype and having extrachromosomal DNA encoding at least the bioB gene product or a functional homolog thereof, is cultured in a media containing desthiobiotin.

The present invention further relates to a method for converting an organism having a biotin retention deficient mutant genotype to an organism having enhanced biotin production by transforming the organism with autonomously replicating extrachromosomal DNA encoding at least one gene product of the biotin operon or a functional homolog thereof.

DETAILED DESCRIPTION

As used herein, the term "biotin retention-deficient mutant genotype" refers to a lesion in birA gene, that produces a change in the birA gene resulting in a decrease in the activity of the birA gene product, that is, a mutation at the birA locus giving rise to a diminished capacity for adenylation of biotin and is hereinafter referred to as birA⁻. A class of preferred lesions in birA comprise lesions which will render the activity of the enzyme dependant on temperature, that is a temperature sensitive birA gene (birA$^{TS}$). Such birA$^{TS}$ mutants decrease the birA function as the temperature of the system increases.

Preferred host cells include biotin-requiring strains (genotype:bio⁻) strains deficient in the repressor of the biotin operon (genotype: bioR⁻) and biotin-requiring strains deficient in the repressor function (genotype: bio⁻, bioR⁻). The most preferred host cells are bioR⁻ strains.

The term "functional homolog of a gene product of the biotin operon" refers to a polypeptide which has the same function as, but which may have the same amino acid sequence as or different in amino acid sequence from, the gene product. Such functional homologs include, for example, polypeptide products of allelic variations of the genes of the biotin operon; analogs and fragments of these polypeptides; and synthetic polypeptides which may be dissimilar in primary structure (amino acid sequence) but which share secondary structures that allow them to possess biological and immunological activities of gene products of the biotin operon [Kaiser, et al., *Science*, 223, 249–255 (1984)].

Figure 1:
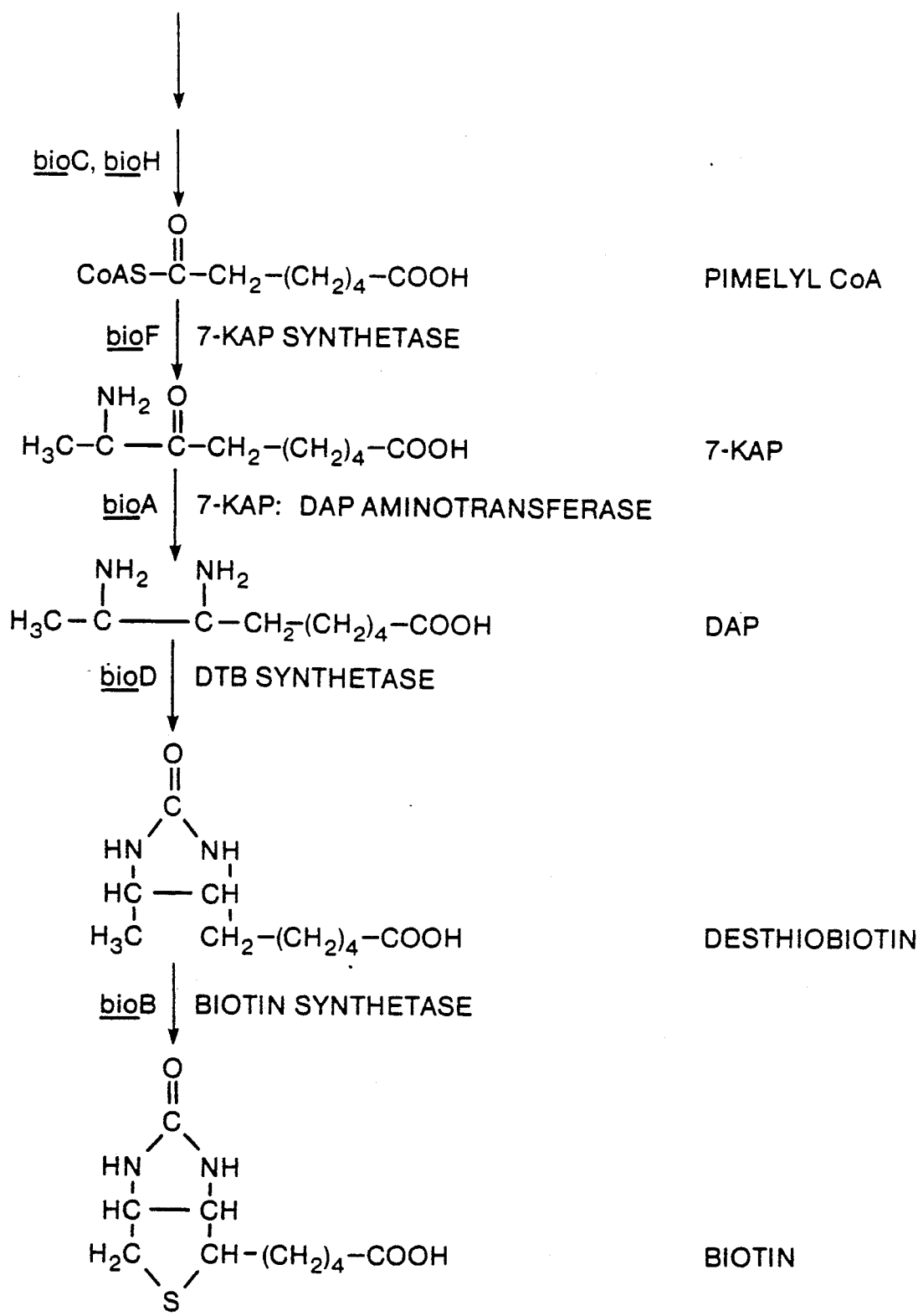
FIG. 1 is a flowchart of the biotin biosynthetic pathway.

A flow chart of biotin biosynthesis is presented in FIG. 1. Six enzymes involved in biotin biosynthesis have been assigned to six genetic loci: bioA, bioB, bioC, bioD, bioF and bioH. Specific reactions catalyzed by bioA, bioB, bioD and bioF gene products have been characterized. Cofactors and substrates for each of these reactions, with the exception of a sulfur atom donor in the last enzymatic step, have been identified. Although the functions of the bioC and bioH gene products have not been characterized due to limitations of crossfeeding studies (wherein biotin-deficient strains obtain survival only by utilizing biotin or by utilizing biosynthetic precursors of biotin excreted by cells with which they are co-cultured), these loci have been identified as essential by genetic complementation.

The six genes coding for biotin synthetic enzymes are located in two regions of the E. coli chromosome. Five of the six genes (bioA, bioB, bioC, bioD and bioF) are contained in a bidirectionally transcribed operon mapped at 17 minutes. BioH is located at 74 minutes. The locations of the genes of the biotin operon and of two other genetic functions which impinge on the biotin biosynthetic pathway, bioR and birA, are given in Table I.

TABLE I

| Genetic Locus | Location on E. coli Chromosome | Proposed Function |
|---|---|---|
| bioA | 17 min | Synthetic enzyme |
| bioB | 17 min | Synthetic enzyme |
| bioC | 17 min | Synthetic enzyme |
| bioD | 17 min | Synthetic enzyme |
| bioF | 17 min | Synthetic enzyme |
| bioH | 74 min | Synthetic enzyme |
| bioR | 88 min | Transcription repressor |
| birA | 88 min | Utilization of biotin |

Figure 2:
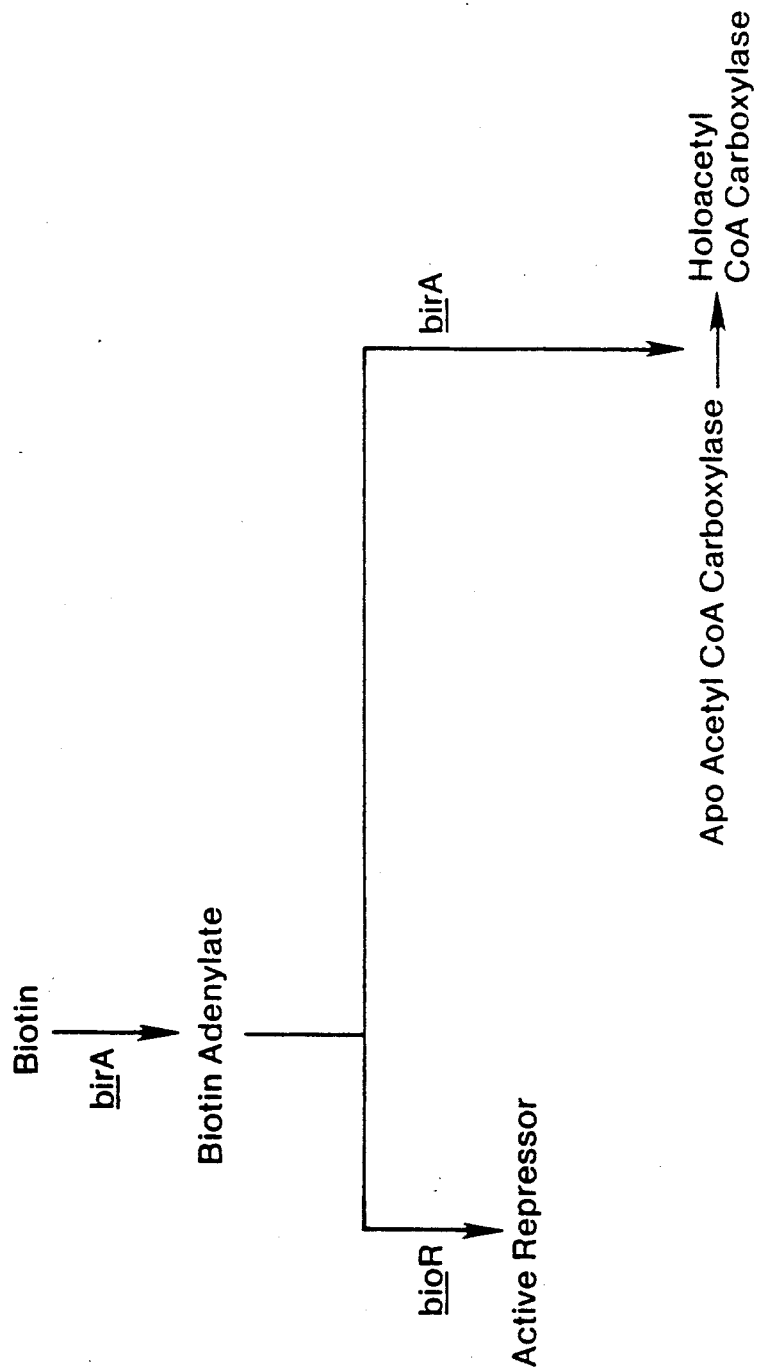
FIG. 2 is a schematic illustration of the bioR and birA gene functions.

Control of biotin synthesis in E. coli is effected at the transcriptional level. After biotin is synthesized, it is adenylated by a product of a gene at a locus designated birA, to form biotinyl-5'-adenylate as illustrated in FIG. 2. A biotin repressor protein, identified as a product of the bioR locus may also bind to biotinyl-5'-adenylate to increase 25-fold the affinity of the bioR gene product for a bio operator. Howard, et. al., Gene, 35, 321-331, (1985), have disclosed that the birA function and the bioR function are effected by the same protein.

Figure 3:
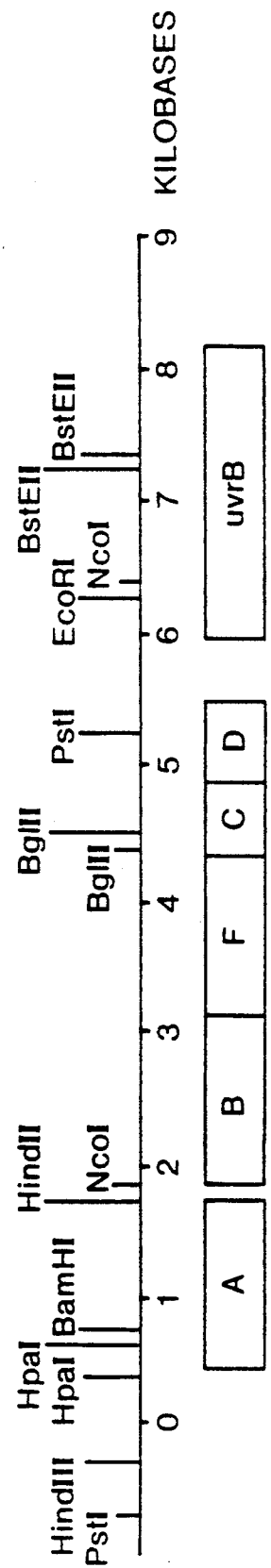
FIG. 3 is a partial restriction map of the bio (A, B, F, C, D) operon and the adjacent uvrB locus on the *E. coli* chromosome.

The bio operator is situated between the bioA structural gene and the bioB structural gene, as depicted in FIG. 3. The bio operator overlaps both the bioA gene promoter and the bioB gene promoter. The bioR gene product may terminate transcription by binding to the bio operator and excluding RNA polymerase from these two divergent promoters.

Biotinyl-5'-adenylate is also a substrate for what is believed to be a third function of the birA gene product, biotin holoenzyme synthetase. Biotin holoenzyme synthetase transfers biotin to acetyl-CoA carboxylase. Acetyl-CoA carboxylase catalyzes a critical step in fatty acid synthesis, which is essential for viability. This implies that a complete elimination of birA activity at the initiation of the fermentation would be lethal. Therefore, at the initiation of the fermentation, it is necessary that sufficient birA activity be present to support growth of the cells. Such birA activity is readily ascertained by one of ordinary skill in the art. Upon completion of the fermentation it is preferred that birA activity is substantially diminished and most preferably eliminated. By employing a birA$^{TS}$ gene, it is possible to regulate the birA function by controlling the temperature of the fermentation system. Therefore as the temperature of the system is increased, the birA function of the cell is decreased.

A genetic locus which maps adjacent to the bioD locus is denominated uvrB. The uvrB gene has no function in biotin physiology, but acts in some way to protect E. coli cells from ultraviolet radiation as reported by Sancar, et al., Cell, 28, 523-530 (1982). Three RNA molecules are transcribed from the urvB locus, one of which may interact with RNA polymerase A. Therefore, if the uvrB gene were multiplied, this interaction may be lethal for an E. coli cell. For this reason, prior to increasing the copy number of a plasmid containing a piece of DNA from the region of the E. coli chromosome which includes the biotin operon, uvrB functions should preferably be eliminated.

In addition to preferably employing a birA$^{TS}$ gene, it is preferred to employ a plasmid having a high copy number, and most preferably a plasmid that exhibits a moderate increase in copy number (40 to 200) upon temperature induction. Such plasmids are described in European Patent Application No. 136,490 and are hereinafter referred to as temperature sensitive plasmids. Therefore when utilizing such temperature sensitive plasmids, it is possible upon increasing the temperature of the reaction to moderately increase the copy number and gene dosage while maintaining cell vitality and decreasing the birA function, thereby resulting in a system capable of producing surprisingly high yields of biotin. The following Examples serve to further illustrate embodiments of the present invention. Although the birA$^-$ strains of Barker, et al., J. Bacteriol., 143, 789-800 (1980) and Campbell, et al., Proc. Natl. Acad. Sci. (USA), 69, 676-680 (1972) are employed in the Examples, other biotin retention deficient strains such as for example the E. coli strain P48 reported in Pai, J.Bacteriol, 112, 1280-1287 (1972), may also be employed.

EXAMPLE 1

Figure 4:
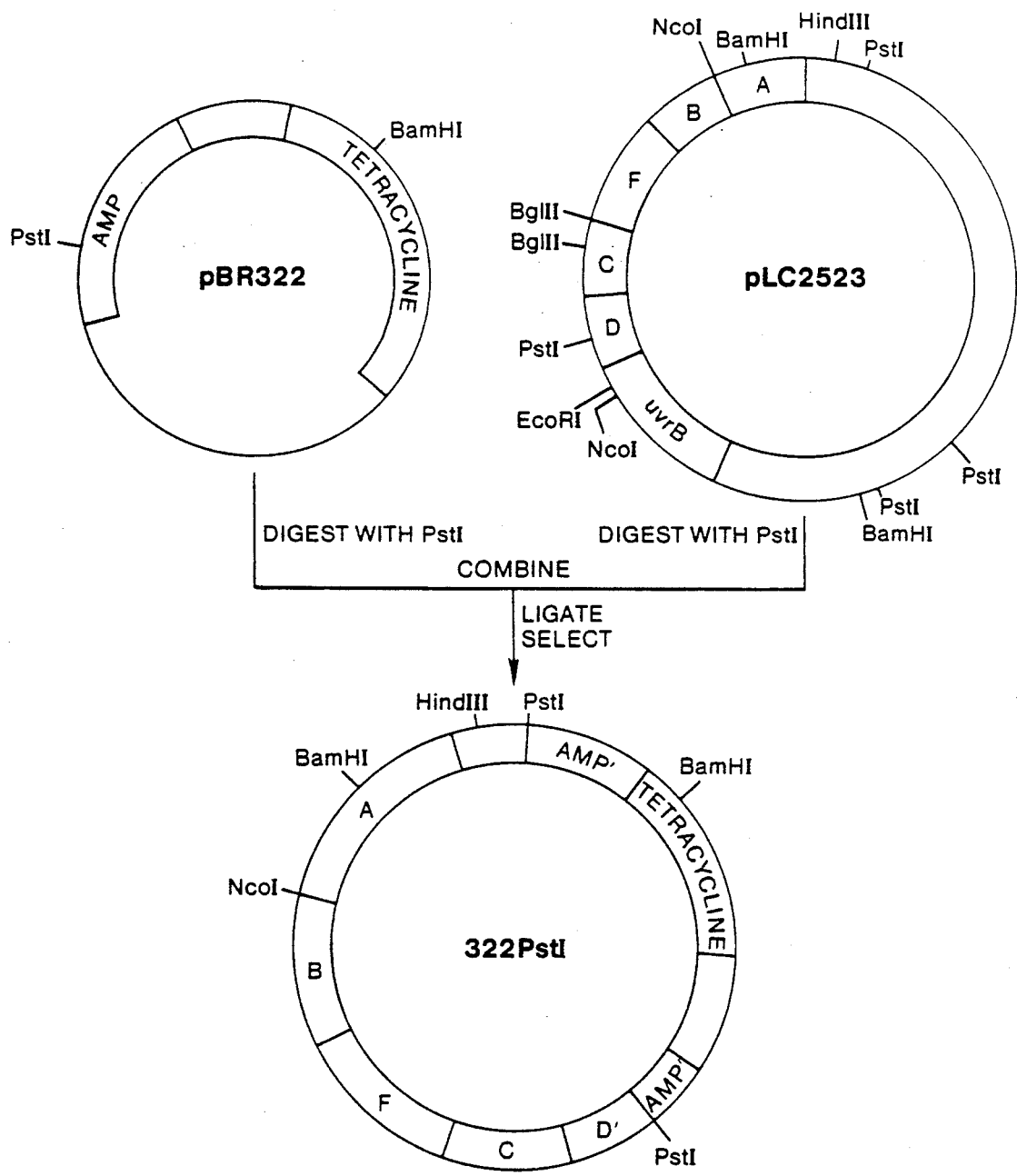
FIG. 4 is a schematic illustration of the construction of the intermediate plasmid 322PstI according to the present invention.

As illustrated in FIG. 4, a first plasmid, designated pLC2523 (deposited August 23, 1985 as Deposit No. A.T.C.C. 53237 with the American Type Culture Collection, 12301 Parklawn Drive, Rockville, Md.) and known to contain the biotin operon (see e.g., Sancar et al., J. Mol. Biol., 148, 63-76, (1981)), and a second plasmid, designated pBR322 (ATCC No. 37017) were digested with PstI and joined by T4 DNA ligase. The mixture was then transformed, according to the procedure of Hanahan, J. Mol. Biol., 166, 557-580 (1983), into bacterial cells of the biotin auxotrophic strain SA291 (bio$^-$, bioR$^+$, birA$^+$) (deposited Aug. 23, 1985 with the American Type Culture Collection, 12301 Parklawn Drive, Rockville, Md., as Deposit No. A.T.C.C. 53236). Colonies were selected on L agar plates containing tetracycline (12 mg/L), which killed any cells that did not contain plasmids having the tetracycline-resistance segment of pBR322. The selected colonies were screened for ampicillin sensitivity, an indication that a PstI digestion fragment from pLC2523 had been inserted into the PstI site of the ampicillin-resistance segment of pBR322, thereby rendering it incapable of conferring resistance.

Restriction fragments of plasmids conferring tetracycline resistance were separated by gel electrophoresis and examined for the presence of fragments having the expected lengths of the biotin operon. In this way it was determined that a plasmid designated 322PSTI contained the biotin operon linked to a tetracycline resistance marker. However, in this plasmid the bioD gene was found not to be intact for it would not complement biotin auxotrophic *E. coli* strain SA291 when grown in the absence of biotin.

Figure 5:
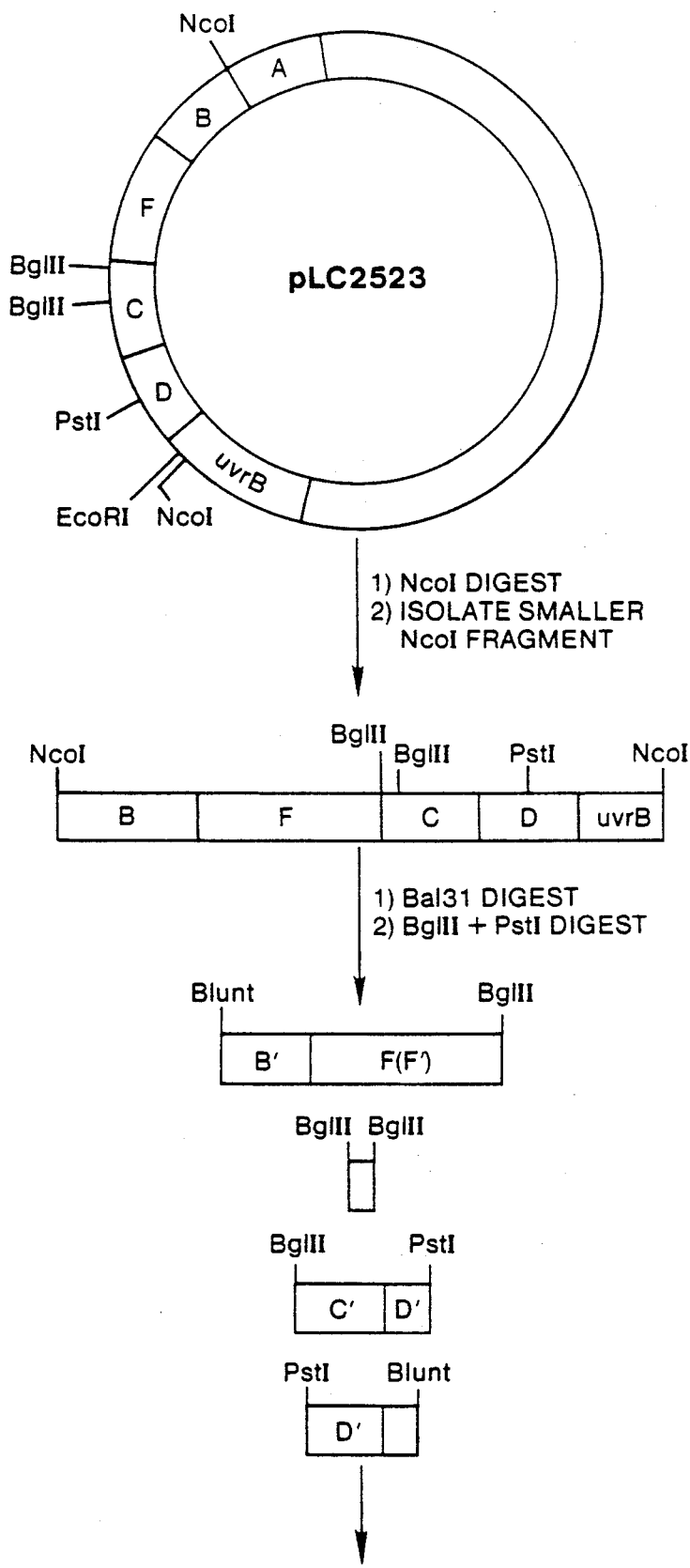
FIG. 5 is a schematic illustration of the construction of a bioD gene restriction fragment according to the present invention.

As illustrated in FIG. 5, in order to obtain the remainder of the bioD gene, pLC2523 was cleaved with NcoI to produce a larger fragment and a smaller fragment (4.4 kilobases in length) which were separated by gel electrophoresis. The smaller fragment was extracted from the gel and both ends of the smaller fragment were digested with the exonuclease BAL31.

In the BAL31 digestion, 30 μg of the restriction fragment was dissolved in 450 μL of BAL31 nuclease buffer containing 0.25 mg/mL of bovine serum albumin. A 200 μL portion was treated with 2 units/μL of BAL31 at 30° C. Samples were withdrawn and phenol extracted at 2.5 min, 5.5 min and 10 min. After ether extraction and ethanol precipitation, an aliquot of each time point sample was analyzed by electrophoresis through a 0.5% (w/v) agarose gel. The three time point samples were pooled. The shortened fragments thus obtained were further cleaved with BglII and PstI. Due to the presence of two BglII sites and one PstI site in the NcoI fragment of pLC2523, four types of fragments were expected. Of these four types of fragments, one was expected to contain the remainder of the bioD gene and to have both a blunt, BAL31-digested end and a cohesive PstI-digested end.

Figure 6:
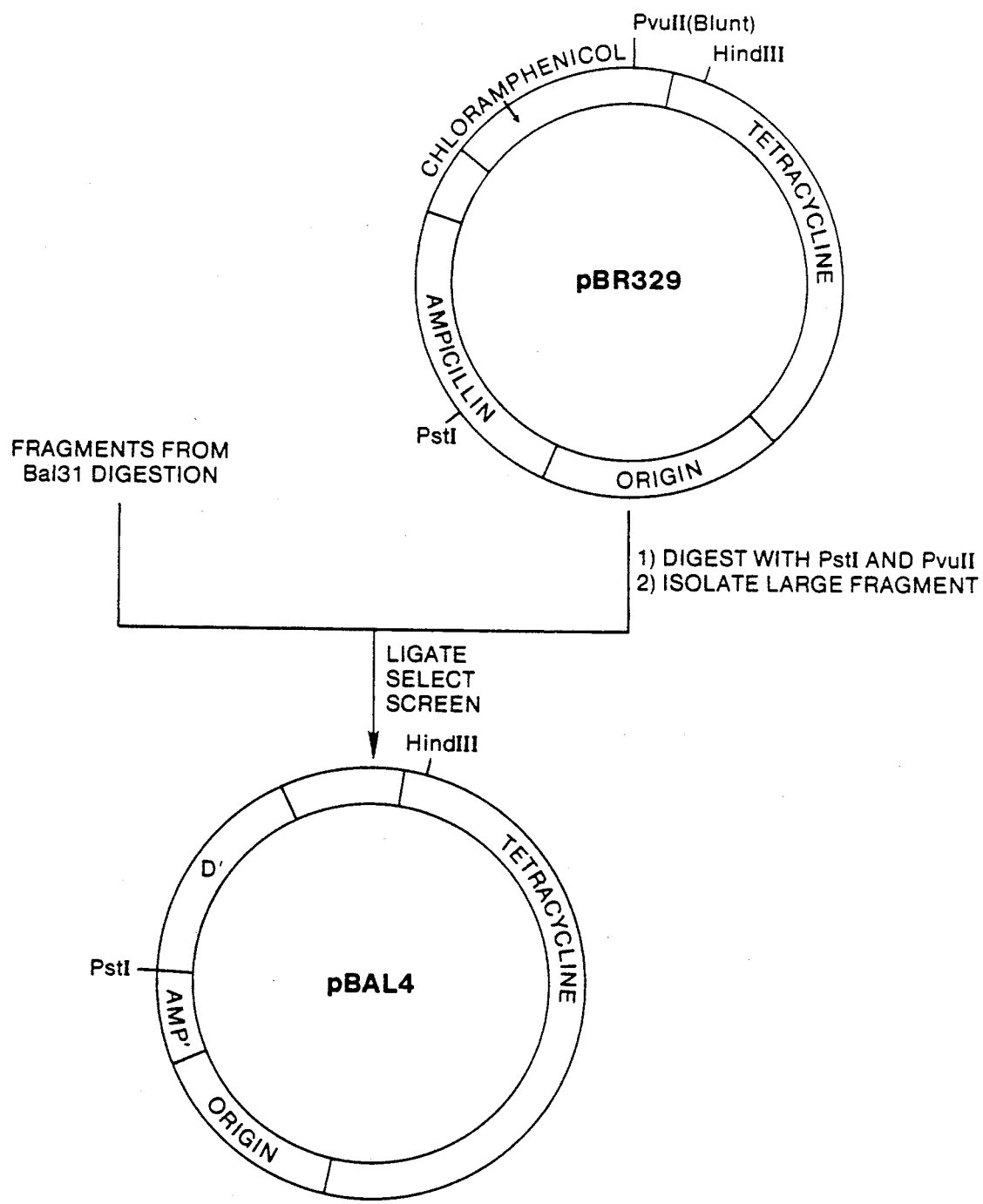
FIG. 6 is a schematic illustration of the construction of the intermediate plasmid pBAL4 according to the present invention.

The plasmid pBR329, [the complete nucleotide sequence of which is published in Covarrubias, et al., *Gene*, 17, 79 (1982), which is incorporated by reference herein] was digested with both PvuII (which cleaves pBR329 in a chloramphenicol-resistance segment, to produce a blunt end) and with PstI (which cleaves pBR329 at a site in an ampicillin-resistance segment) to obtain two pieces which were separated by gel electrophoresis. The larger of the pieces (containing a tetracycline resistance segment and an origin of replication) was mixed with the four types of fragments produced by the BglII and PstI digestion of the 4.4 kb NcoI fragment described above in the presence of T4 DNA ligase. As shown in FIG. 6, only those fragments containing the remainder of the bioD gene had the combination of blunt and PstI-digested ends required to join with the larger PvuII/PstI fragment from pBR329 to form a cyclic plasmid designated pBAL4.

Bacteria of strain SA291 were transformed with the products of the ligation with the larger fragment of pBR329. Colonies were selected for tetracycline resistance, screened for ampicillin sensitivity and screened for chloramphenicol sensitivity. The lengths of the inserts in various plasmids were determined by restriction endonuclease analysis.

Figure 7:
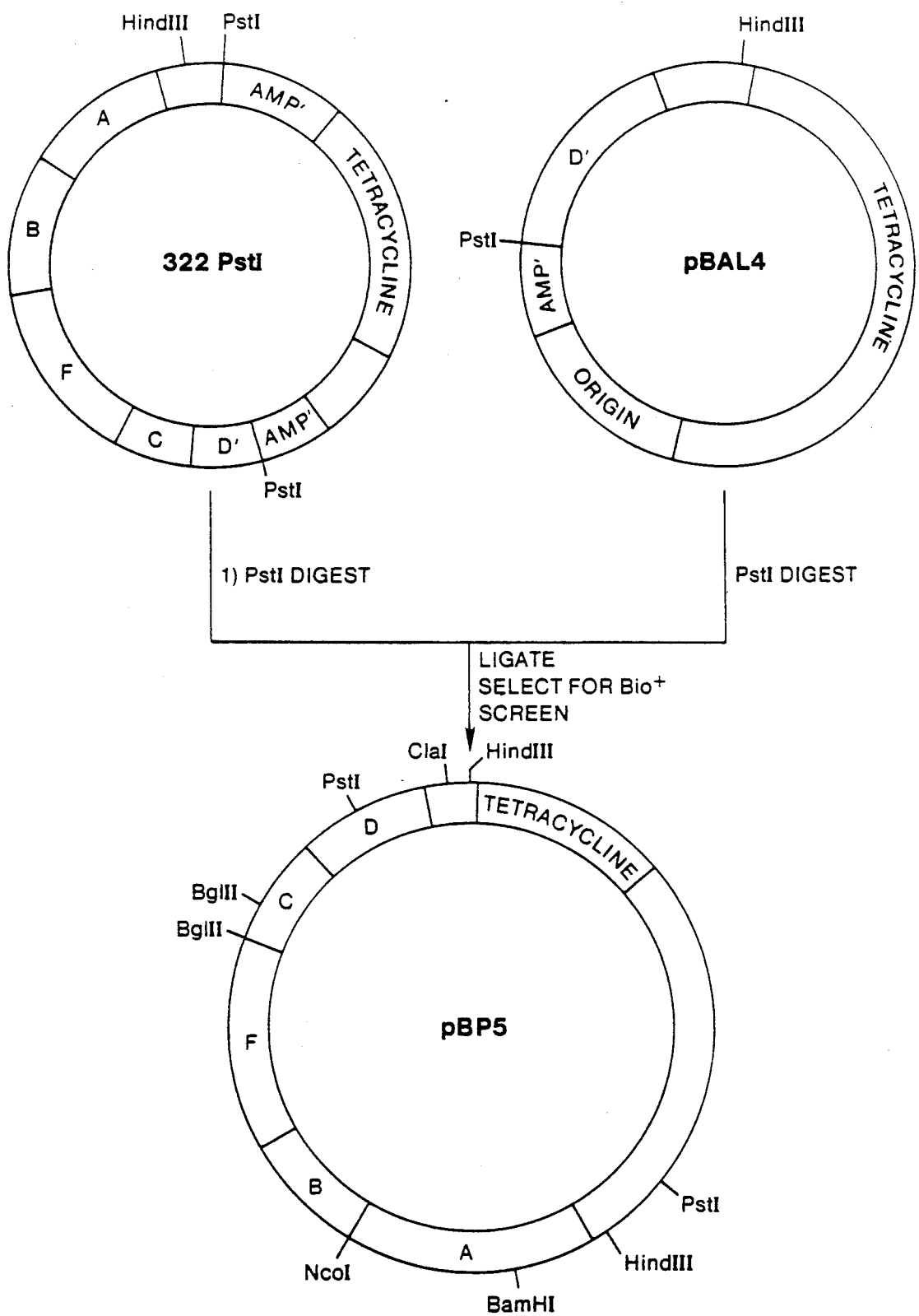
FIG. 7 is a schematic illustration of the construction of the biotin operon-containing plasmid pBP5 according to the present invention.

As shown in FIG. 7, the plasmids 322PstI and pBAL4 were separately digested with PstI. These digests were combined in a ligation reaction, using T4 DNA ligase. The resulting mixture was used to transform the cells of strain SA291. Colonies were selected for a combination of growth in the absence of biotin and growth in the presence of 12 mg/mL tetracycline. Presence of the complete bio operon was confirmed by retransformation of plasmid-free SA291 in conjunction with restriction endonuclease digestion analysis. A resulting plasmid, designated pBP5, contained all of the genes of the biotin operon: genes bioA, bioB, bioF, bioC and the portion of the bioD gene upstream of the PstI site derived from 322PstI and the portion of the bioD gene downstream of the PstI site derived from pBAL4.

Next, the temperature sensitive copy number plasmid pCFM 526 was digested with EcoRI and resealed with ligase to produce pCFM 526ΔE4, which lacked the $P_L$ promoter contained in pCFM 526. Plasmid pCFM526 had been constructed as described in Morris, published European Patent Application No. 136,490, from plasmid pCFM414 (ATCC No. 40,076).

Figure 8:
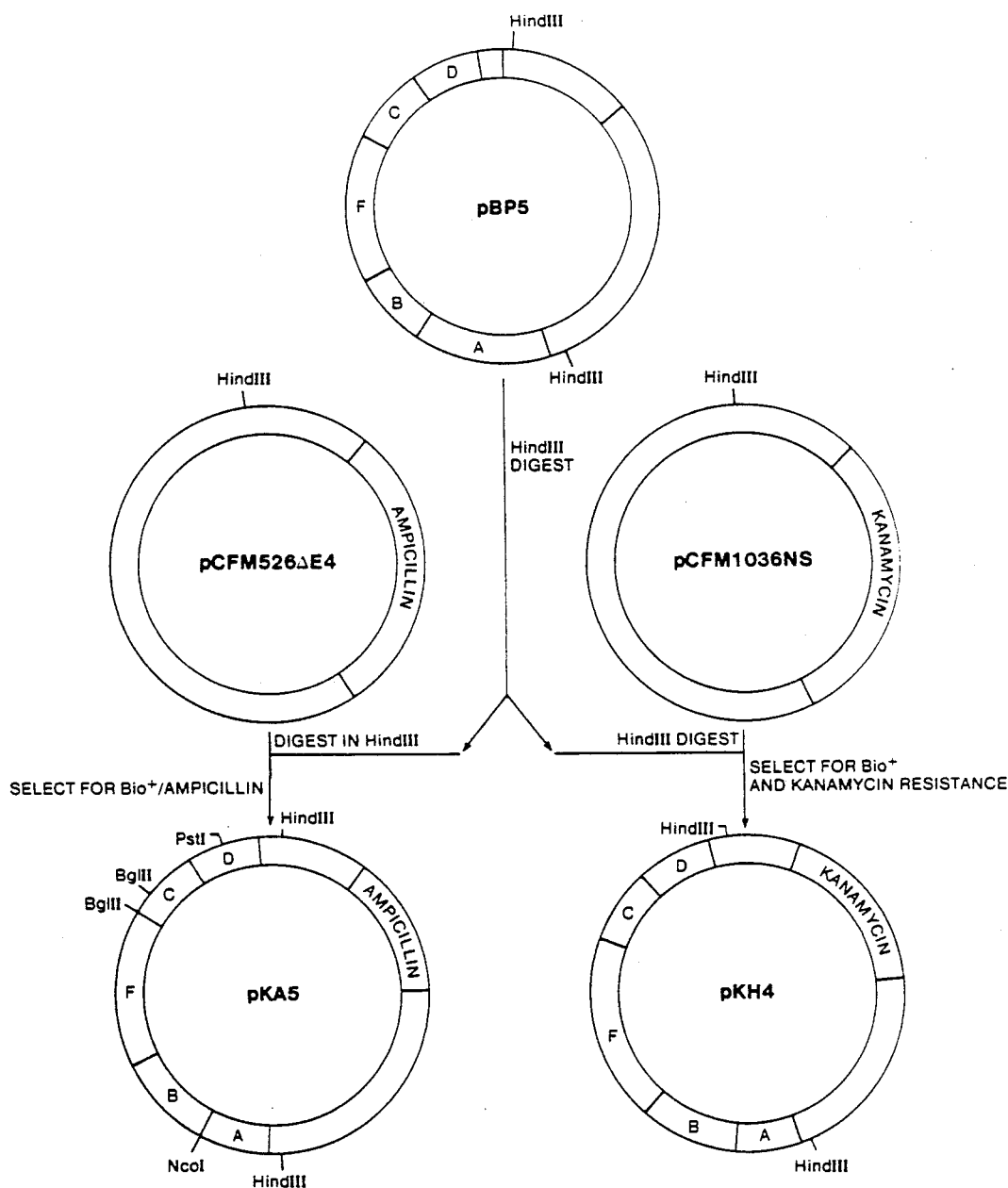
FIG. 8 is a schematic illustration of the construction of the plasmids pKA5 and pKH4 according to the present invention.

As shown in FIG. 8, plasmid pCFM526ΔE4 and the plasmid pBP5 were separately digested with HindIII. The fragments were ligated and used to transform SA291. Colonies were selected for ampicillin resistance and the ability to grow in the absence of biotin. A plasmid designated pKA5 was isolated. This plasmid contained the five genes of the bio operon linked to a temperature inducible origin of replication.

EXAMPLE 2

As further shown in FIG. 8, another plasmid was also constructed in a fashion analogous to the construction of pKA5 described in Example 1, but with the substitution of a plasmid designated pCFM1036NS, which contains a kanamycin resistance segment, for pCFM526ΔE4. Colonies were therefore selected for kanamycin resistance instead of ampicillin resistance to obtain cells bearing a plasmid pKH4.

EXAMPLE 3

A HindIII fragment from pBP5 was treated with BAL31 and the mixture was ligated into HpaI-cut pCFM526ΔE4. Colonies were selected for biotin production, ampicillin resistance, and tetracycline sensitivity. Three plasmids, pBA2, pBA4 and pBA6 were obtained from this selection.

EXAMPLE 4

Figure 9:
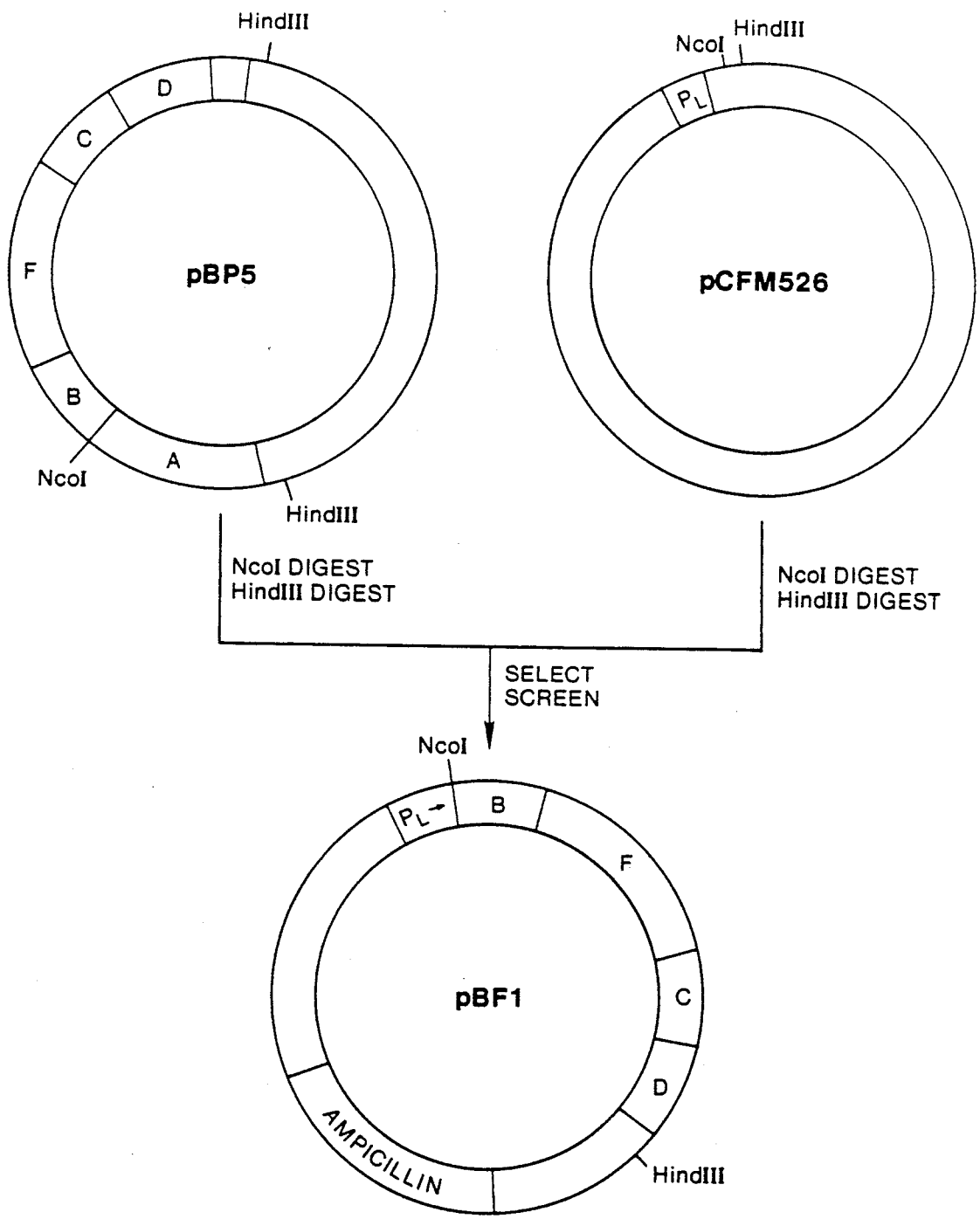
FIG. 9 is a schematic illustration of the construction of the plasmid pBF1 according to the present invention.

As illustrated in FIG. 9, the plasmids pBP5 and pCFM526 were cut with NcoI and HindIII. The ligation product of these digests was transformed into an *E. coli* strain AM7 containing plasmid pMW1 (A.T.C.C. No. 39933) harboring a gene for the temperature sensitive repressor $CI^{857}$. In this construction, designated pBF1, the bioB gene is placed under the control of the $P_L$ promoter. Therefore, this construction is useful for converting desthiobiotin into biotin by means of the bioB gene product, biotin synthetase.

EXAMPLE 5

The plasmid pLC2523 was digested with HindIII and NcoI. The plasmid pCFM526 was similarly cut. A ligation product of these two digests, designated pAHN203, was transformed into cells of a bacterial strain containing the temperature-sensitive repressor of bacteriophage λ ($CI^{857}$). The plasmid pCFM526 contains the $P_L$ promoter of bacteriophage λ. A gene or genes inserted downstream from this locus are controlled by this promoter. The promoter activity is regulated by repressor $CI^{857}$. Therefore, when the temperature is raised, the repressor function is eliminated, the promoter is activated and the desired gene products are expressed. See e.g., Morris, supra. In pAHN203 the bioA gene is under $P_L$ control. The plasmid pAHN203 is combined with pBF1 to produce a plasmid which produces biotin under $P_L$ control.

The following buffers were employed in the Examples. A high salt buffer comprising: 75 mM NaCl; 50 mM Tris-HCl, pH 7.6; 10 mM MgCl$_2$; and 5 mM dithiothreitol. A medium salt buffer comprising: 37.5 mM NaCl; 30 mM Tris-HCl, pH 7.6; 10 mM MgCl$_2$; and 5 mM dithiothreitol. A low salt buffer comprising: 10 mM Tris-HCl, pH 7.6; 10 mM MgCl$_2$; 20 mM KCl; and 5 mM dithiothreitol. A ligase buffer comprising: 50 mM Hepes, pH 7.5; 10 mM MgCl$_2$; 5 mM dithiothreitol; and 0.4 mM adenosine triphosphate. A polynucleotide kinase buffer comprising: 50 mM Tris-HCl, pH 7.6; 10 mM MgCl$_2$; 1 mM spermidine; 5 mM dithiothreitol; and 0.1 mM ethylenediamine tetraacetic acid (EDTA). A BAL31 nuclease buffer comprising 12 mM CaCl$_2$; 12 mM MgCl$_2$; 200 mM NaCl; 20 mM Tris-HCl, pH 8.0; and 1 mM EDTA.

The restriction enzymes EcoRI and NcoI were used in the high salt buffer and were obtained from New England Biolabs, Beverly, Mass. The restriction enzymes BglII, BamHI, HindIII and PstI were used in medium salt buffer and were obtained from New England Biolabs, Beverly, Mass. The restriction enzyme HpaI was used in the low salt buffer. The DNA ligase was used in ligase buffer and was obtained from New England Biolabs, Beverly, Mass. The nuclease BAL31 was used in BAL31 nuclease buffer and was obtained from Bethesda Research Laboratories, Gaithersburg, Md. Bovine serum albumin was also obtained from Bethesda Research Laboratories.

Ampicillin, kanamycin sulfate, chloramphenicol and tetracycline were obtained from Sigma Chemical Company (Sigma), St. Louis, Mo. Desthiobiotin was also obtained from Sigma Chemical Company. Biotin was obtained from either Sigma or from J. T. Baker Chemical Company, Phillipsburg, N.J. Strain BM4062 which has been deposited (Aug. 23, 1985) with the American Type Culture Collection, 12301 Parklawn Drive, Rockville, Md. as A.T.C.C. 53238, had lesions in the bioR function and the birA function. The birA mutants were temperature sensitive in that they were viable at low temperatures (~28° C.) but unable to grow at high temperatures (~43° C.). Depending on the specific mutant in question, the lethal effect of high temperature could be reversed by adding exogenous biotin. The other plasmids and strains employed in the Examples are summarized in Table II. Except for SA291, all of the birA$^-$ strains listed in Table II are reported in Barker et al., *J. Bacteriol.*, 143, 789-800(1980) or Campbell, et al., *Proc. Natl. Acad. Sci.* (USA), 69, 676-680 (1972) wherein they are all described as biotin requiring strains. Strain SA291 has been reported in Cleary, et al., *J. Bacteriol.*, 112, 830-839 (1972). In Table II, it should also be noted that BioRP refers to a genotype giving rise to a "partially defective" BioR gene product.

The following assays were utilized to determine the biotin concentration of the samples in the following Examples.

Microbiological Assay

The biotin concentration was determined by "cross-feeding" SA291 cells with the biotin produced by the designated strain. Initially, SA291 was cultured overnight in GMH broth (9 g/L vitamin assay Casamino Acids (Difco, Detroit, Mich.); 4 g/L glucose;20 μg/L l-histidine;40 μg/L thiamine; 1 mM MgSO$_4$; 6 g/L Na2HPO$_4$; 3 g/L KH$_2$PO$_4$; 0.5 g/L NaCl; and 1 g/L NH$_4$Cl) supplemented with 300 pM d-biotin (50 ml volume) at 37° C. The overnight culture was diluted 400 fold in GMH broth. 2 mL samples of diluted culture were dispensed into test tubes. Varying concentrations of the sample to be analyzed were added to the tubes. The assay was standardized by adding one each of the following concentrations of d-biotin (Sigma Chemical Company, St. Louis, Mo.) to six individual tubes: 30 pM, 100 pM, 300 pM, 1000 pM, 3000 pM added d-biotin. All tubes were cultured overnight at 37° C. The optical density of resulting cultures were determined and the unknowns were correlated with the standards.

Spectrophotometric Assay

The biotin concentration was determined by a biotin spectrophotometric assay derived from McCormick et al., *Analytical Biochemistry*, 34, 226-236 (1970). Specifically, 100 microliters of sample were transferred to a test tube to which 900 microliters of water were added. Concentrated H$_2$SO$_4$ (5 microliters) was added to reduce the pH of the solution to less than 2. To the solution was added 1 mL of n-butanol and the resulting solution was vortexed for one minute and then centrifuged for one minute at 3200 rpm. The upper, butanol phase of the solution was then transferred to a 1.5 mL Eppendorf tube. The solvent was evaporated to dryness before the addition of 100 microliters of 2% (v/v) sulfuric acid and 100 microliters of 0.2% (w/v) 4-dimethylaminocinnamaldehyde. The resulting solution was vortexed and then allowed to stand undisturbed for 5-10 minutes before the addition of 800 μl of ethanol. The absorbance (A) of the solution at 532 nm was determined on a Gilford Response spectrophotometer. From the absorbance, the biotin concentration (C) in moles/-liter was obtained for the 1 cm path length from the equation:

$$C = (5.7 \times 10^{-5})A$$

EXAMPLE 5

The various cultures utilized in Examples 6 and 7 were constructed by transforming an appropriate host strain with a plasmid derived from Examples 1 or 2. accordance with the procedures described by Hanahan, supra. The host strains and plasmids utilized are listed in Table II.

EXAMPLE 6

Flask Method

A flask containing 30 mL of GMH broth was inoculated with a volume of a culture listed in Table II. The resulting cultures were incubated with shaking at 37° C. At 0 hr, 6 hr, 21 hr, 30 hr and 45 hr, an aliquot was removed and filter sterilized. (A 2.5 mL aliquot was removed at 0 hr, while 1 mL aliquots were removed at the other time points). The sterilized samples were assayed in accordance with the microbiological assay previously described and the results (Run Nos. 1-7) are illustrated in Table II.

EXAMPLE 7

Fermentor Method

The appropriate host bearing plasmids were cultured overnight in GMH broth. A 10 mL aliquot of the culture was added to 1000 ml. of GMH broth supplemented with 20 mL of 1% alanine, 20 mL of 1% methionine, 20 mL of 0.7% cysteine and appropriate antibiotic (final concentration of 50mg/L ampicillin was used when plasmid pKA5 was employed and 25 mg/L of kanamycin sulfate was used when plamid pKH4 was employed. The fermentation was performed in a New Brunswick Bio-Flo fermentor with the following features: 1) constant agitation at 600 rpm; 2) sprarging with air; 3) pH control between 6.8 and 7.2 by automatic addition of concentrated ammonia hydroxide; 4) temperature control and 5) a slow feed during the course of the fermentation. Dissolved oxygen and carbon dioxide evolution were not monitored. The feed consisted of: 12% glucose; 0.6% vitamin assay casamino acids, 35 µM magnesium sulfate, 0.2% alanine, 0.2% methionine, 0.12% cysteine, 7 µM sodium molybdate and half strength M9 minimal salts. The feed was initiated eight hours after innoculation at a continuous rate of 14 mL/hr. The temperature at the time of innoculation was 30° C. When the optical density of the culture reached approximately 10, measured at 600 nanometers, the temperature was incrementally raised to 40° C. The biotin concentrations reported in Table II were determined 24 hours after innoculation using either the microbiological assay (Run Nos. 8, 9 and 10) or the spectrophotometric assay (Run Nos. 10 and 12).

EXAMPLE 8

Cultures used in this Example are described in Table III.

TABLE III

| Strain | Genotype | Culture Plasmid | Genotype |
|---|---|---|---|
| FM6 | bio$^-$, bioR$^-$, birA$^-$ | None | — |
| FM6 | bio$^+$, bioR$^+$, birA$^+$ | pKA5 | bio$^+$ |
| S965 | bio$^+$, bioR$^P$, birA$^{TS}$ | None | — |
| S965 | bio$^+$, bioR$^P$, birA$^{TS}$ | pKA5 | bio$^+$ |
| BM4062 | bio$^-$, bioR$^-$, birA$^{TS}$ | None | — |
| BM4062 | bio$^-$, bioR$^-$, birA$^{TS}$ | pKA5 | bio$^+$ |

Each culture was inoculated into Luria broth (1.0% casamino acids, 0.5% yeast extracts, 0.5% sodium chloride) and incubated overnight at 30° C. The optical density of each culture was determined and represented in Table IV. A ten-fold dilution was necessary due to density of the culture.

TABLE IV

Culture

TABLE II

| | | Biotin Production Determined by Bioassay | | | | |
|---|---|---|---|---|---|---|
| Run No. | Host Strain | Relevant Genotype | Plasmid | Relevant Genotype | Fermentation Method | Concentration of Biotin |
| 1 | SA291 | bio$^-$ bioR$^-$ birA$^+$ | pBP5 | bio$^+$ | Flask | 200 nM (50 µg/L) |
| 2 | S965 | bio$^+$ bioR$^P$ birA$^{TS}$ | pBP5 | bio$^+$ | Flask | 600 nM-1000 nM (150-250 µg/L) |
| 3 | BM4110 | bio$^-$ bioR$^-$ birA$^+$ | pBP5 | bio$^+$ | Flask | 200 nM (50 µg/L) |
| 4 | BM4086 | bio$^-$ bioR$^-$ birA$^+$ | pBP5 | bio$^+$ | Flask | 100 nM (25 µg/L) |
| 5 | BM4084 | bio$^-$ bioR$^-$ birA$^+$ | pBP5 | bio$^+$ | Flask | 300 nM (75 µg/L) |
| 6 | BM4062 | bio$^-$ bioR$^-$ birA$^{TS}$ | pKH4 | bio$^+$ | Flask | 2–6 µM (0.5–1.5 mg/L) |
| 7 | BM4062 | bio$^-$ bioR$^-$ birA$^{TS}$ | pKA5 | bio$^+$ | Flask | 2–6 µM (0.5–1.5 mg/L) |
| 8 | S965 | bio$^+$ bioR$^P$ birA$^{TS}$ | pBP5 | bio$^+$ | Fermentor | 6–10 µM (1.5–2.5 mg/L) |
| 9 | BM4062 | bio$^-$ bioR$^-$ birA$^{TS}$ | pKA5 | bio$^+$ | Fermentor | 80 µM (20 mg/L) |
| 10 | BM4062 | bio$^-$ bioR$^-$ birA$^{TS}$ | pKA5 | bio$^+$ | Fermentor | 125 µM (30 mg/L) |
| 11 | BM4062 | bio$^-$ bioR$^-$ birA$^{TS}$ | pKH4 | bio$^+$ | Fermentor | 50 µM (12 mg/L) |
| 12 | BM4062 | bio$^-$ bioR$^-$ birA$^{TS}$ | pKH4 | bio$^+$ | Fermentor | 80 µM (20 mg/L) |

Although differences among assays for biotin make a direct comparison difficult, a comparison of the results reported in Table II with medium concentrations of biotin reported for wild type and mutant *E. coli* serve to illustrate the improvement in biotin production afforded by the present invention. For example, according to Campbell, et al., *Proc. Natl. Acad. Sci. (USA)*, 69, 676–680 (1972), the media concentration of biotin for wild type *E. coli* is less than 0.05 nM and for strain S942 (a birA$^-$ strain) is 30–90 nM. According to Pai, *J. Bacteriol.*, 112, 1280–1287 (1972), for a strain P48, which may be employed as a biotin retention deficient mutant strain according to the present invention, the media concentration of biotin is 1000 times that of the wild type.

| Strain | Plasmid | $A^{600}/10$ | $A^{600}$ | Inoculum |
|---|---|---|---|---|
| FM6 | None | 0.6205 | 6.205 | 5 µL |
| FM6 | pKA5 | 0.6056 | 6.056 | 5 µL |
| BM4062 | None | 0.2919 | 2.919 | 10 µL |
| BM4062 | pKA5 | 0.5768 | 5.768 | 5 µL |
| S965 | None | 0.4920 | 4.920 | 6 µL |
| S965 | pKA5 | 0.4379 | 4.379 | 7 µL |

A flask containing 30 mL of GMH broth was inoculated with the volume of the six cultures listed in the Table IV above. The resulting cultures were incubated with shaking at 37° C. At 0 hr, 6 hr, 21 hr, 30 hr and 45 hr an aliquot was removed and filter sterilized. (A 2.5 mL aliquot was removed at 0 hr, while 1 mL aliquots were removed at the other time points). The sterilized samples were assayed in accordance with the microbiological assay previously described and the results are illustrated in Table V.

TABLE V

| | Biotin Concentration Time Dependence of Biotin Accumlation | | | | |
|---|---|---|---|---|---|
| | Culture | | | | |
| Strain/Plasmid | 0 hr | 6 hr | 21 hr | 30 hr | 45 hr |
| FM6 | <0.5 nM | (1) | <1.6 nM | <1.6 nM | <1.6 nM |
| FM6/pKA5 | <0.5 nM | <1 nM | 12 nM | 17 nM | 6.7 nM |
| S965 | <1.6 nM | 13 nM | 133 nM | 140 nM | 137 nM |
| S965/pKA5 | <1.6 nM | 43 nM | 150 nM | 173 nM | 143 nM |
| BM4062 | <0.5 nM | <1.6 nM | <1.6 nM | <1.6 nM | <1.6 nM |

TABLE V-continued

| | Biotin Concentration Time Dependence of Biotin Accumlation | | | | |
|---|---|---|---|---|---|
| | Culture | | | | |
| Strain/Plasmid | 0 hr | 6 hr | 21 hr | 30 hr | 45 hr |
| BM4062/pKA5 | <1.6 nM | (2) | 3.1 μM | 3.2 μM | 1.5 μM |

(1) Time point was contaminated; no value obtainable.
(2) No data point in the linear range of the assay.

While the present invention has been described in terms of preferred embodiments, it is understood that variations and improvements will occur to those skilled in the art. Therefore, it is intended that the appended claims cover all such equivalent variations which come within the scope of the invention as claimed.

What is claimed is:

1. A system for the production of biotin comprising:
   an Escherichia coli cell having a biotin retention-deficient mutant genotype: and
   nonlytic extrachromosomal DNA, within said cell, encoding at least one gene product of the biotin operon of Escherichia coli or a functional homolog thereof and having a uvrB$^-$ genotype.

2. The system as recited in claim 1 wherein said biotin retention-deficient mutant genotype is birA$^-$.

3. The system as recited in claim 2 wherein said biotin retention-deficient mutant genotype is birA$^{TS}$.

4. The system as recited in claim 3 wherein said extrachromosomal DNA encodes the biotin operon of Escherichia coli.

5. The system as recited in claim 4 wherein said cell has a bioR$^-$ genotype.

6. The system as recited in claim 4 wherein said cell has a bio$^-$ genotype.

7. The system as recited in claim 1 wherein said extrachromosomal DNA encodes biotin synthetase or a functional homolog thereof.

8. The system as recited in claim 7 wherein said cell has a birA$^-$ genotype.

9. The system as recited in claim 8 wherein said cell has a bioR$^-$ genotype.

10. The system as recited in claim 9 wherein said cell has a bio$^-$ genotype.

11. The system as recited in claim 10 wherein said bioA$^-$ genotype is birA$^{TS}$.

12. A system for the production of biotin comprising:
    an Escherichia coli cell having a (bio$^-$, birA$^-$, bioR$^-$) genotype; and
    extrachromosomal DNA, within said cell, encoding the biotin operon of Escherichia coli and having a uvrB$^-$ genotype.

13. The system as recited in claim 12 wherein said cell has a (bio$^-$, birA$^{TS}$, bioR$^-$) genotype.

14. A method for converting an Escherichia coli cell, having a biotin retention deficient mutant genotype to an Escherichia coli cell having enhanced biotin production, comprising the steps of:
    transforming the organism with autonomously replicating, nonlytic extrachromosomal DNA having a uvrB$^-$ genotype and encoding a gene product of the biotin operon or a functional homolog thereof.

15. A method for converting desthiobiotin to biotin comprising the steps of:
    culturing an Escherichia coli cell, having a biotin retention-deficient mutant genotype and having nonlytic extrachromosomal DNA with a uvrB$^-$ genotype encoding a bioB gene product of the biotin operon of Escherichia coli or a functional homolog thereof, in a medium comprising desthiobiotin.

* * * * *